United States Patent [19]

Wood et al.

[11] Patent Number: 4,639,334

[45] Date of Patent: Jan. 27, 1987

[54] PREPARATION OF 1-BENZYLAZETIDINE-3-OL DERIVATIVES

[75] Inventors: Derek A. Wood, Sittingbourne; Paul H. Briner, Faversham, both of England

[73] Assignee: Shell Oil Company, Houston, Tex.

[21] Appl. No.: 732,214

[22] Filed: May 9, 1985

[30] Foreign Application Priority Data

May 18, 1984 [GB] United Kingdom ................. 8412814

[51] Int. Cl.$^4$ ........................................... C07D 205/04
[52] U.S. Cl. .................................................. 548/952
[58] Field of Search ................................ 260/239 AR

[56] References Cited

U.S. PATENT DOCUMENTS 4,560,507 12/1985 Orr .................................. 260/239 A

FOREIGN PATENT DOCUMENTS 140437 5/1985 European Pat. Off. ...... 260/239 AR
1014404 1/1958 Fed. Rep. of Germany ...... 260/239 AR

OTHER PUBLICATIONS

Chatterjee et al., Chemical Communications, (1968), p. 93.

Primary Examiner—Donald G. Daus
Assistant Examiner—William A. Teoli, Jr.

[57] ABSTRACT

A process for the preparation of 1-substituted azetidin-3-ol derivatives of the formula:

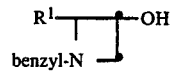

in which $R^1$ represents a hydrogen atom or an alkyl, aryl or aralkyl group in which the alkyl moiety contains up to eight carbon atoms, by cyclizing a solution in triethylamine of an aminoalcohol of the formula:

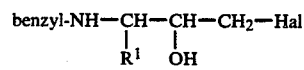

in which Hal represents a halogen atom and the use of such derivatives as intermediates for the preparation of azetidine-3-carboxylic acid derivatives.

5 Claims, No Drawings

PREPARATION OF 1-BENZYLAZETIDINE-3-OL DERIVATIVES

BACKGROUND OF THE INVENTION

Carboxyazetidine is of interest for selectively sterilizing the male parts of plants: European patent application 29265. It can be prepared from 1-benzhydrylazetidine-3-ol, which is prepared by the reaction of epichlorohydrin with benzhydrylamine: A. G. Anderson, Jr. and R. Lok, Journal of Organic Chemistry, 1972, volume 37, pages 3953–5. However, the introduction of a benzhydryl group is very inconvenient for an economically practicable synthesis route, since the size of that group greatly increases the bulk of material to be processed, only to be removed once its protective function is no longer required. It would be economically very desirable to use a protective group less bulky than the benzhydryl group, for example, the benzyl group, but previous attempts to react epichlorohydrin with benzylamine have failed to produce any significant yield of the desired cyclized azetidine product.

Applicant's coworker found that the use of an aqueous reaction medium enables useful yields of 1-substituted azetidines to be obtained from an epoxy halide and less bulky amines such as benzylamine, which process forms the subject of his U.S. Pat. No. 4,560,507. The experiments described in that patent application demonstrate that no azetidine formation occurs when using organic solvents such as acetonitrile, methanol, butanol or ethanediol as reaction medium, but cyclization to an azetidine was achieved by the use of an aqueous reaction medium.

DESCRIPTION OF THE INVENTION

Applicants have now surprisingly found that, although previous work with organic solvents failed to achieve cyclization, replacement of the aqueous reaction medium by triethylamine as solvent not only produces the cyclized azetidine, but gives this product in significantly improved yields. Moreover, triethylamine has been found to be unexpectedly specific in producing this yield increase; using other tertiary alkylamines failed to produce any azetidine product. Also, triethylamine is not only apparently unique in its promotion of the cyclization reaction, it is also commercially very convenient because its boiling point (89° C.) is convenient for reflux operation. Further, it has been found that triethylamine effectively removes the hydrogen halide generated during the cyclization reaction, precipitating the amine hydrohalide, and moreover this precipitate carries with it any non-cyclized polymer which is sometimes formed as an unwanted by-product in the cyclization reaction.

Accordingly, the invention provides a process for the preparation of 1-substituted azetidin-3-ol derivatives of the formula:

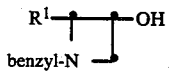 (I)

in which $R^1$ represents a hydrogen atom or an alkyl, phenyl or phenalkyl group, in which the alkyl moiety contains up to 8 carbon atoms, by cyclizing a solution in triethylamine of an aminoalcohol of the formula

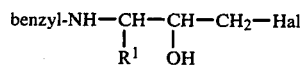 (II)

in which Hal represents a halogen atom.

Preferably $R^1$ represents a hydrogen atom and Hal represents a chlorine atom.

The cyclization of the aminoalcohol II to the azetidine I is suitably carried out at an elevated temperature, for example from 50° to 150° C., preferably under reflux at the boiling point of the reaction mixture. It has also been found that the cyclization reaction can be usefully accelerated by the inclusion of a phase transfer catalyst, particularly those containing iodide ions. Suitable phase transfer catalysts include tetraalkylammonium halides, especially iodides, such as tetrabutylammonium iodide. The amount of catalyst is not critical; the lower limit at which a useful rate increase is attained usually being 0.1 mole percent, and the upper limit usually being determined by solubility in the triethylamine reaction medium, generally being about 1.6 mole percent.

The starting aminoalcohol of formula II is conveniently prepared as described in co-pending application No. 604696, namely by reacting an epoxy halide of the formula:

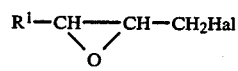 (III)

with benzylamine. This reaction can be carried out by mixing the reactants in an organic solvent, for example a hydrocarbon solvent such as cyclohexane. Suitable reaction temperatures are from 10° C. to 50° C. and suitable reaction times are from 12 to 36 hours. The amino-alcohol of formula IV may be recovered from the reaction mixture by conventional procedures and, if desired, may be purified, for example by recrystallization, before cyclization.

As mentioned above, the 1-benzylazetidin-3-ol derivatives of formula I are useful intermediates. Thus, they may be converted by known procedures, for example, via the corresponding 3-cyanoazetidine derivative, to azetidine-3-carboxylic acid derivatives, which exhibit plant growth regulant properties, especially the property of rendering sterile the male parts of plants.

The invention therefore includes the use of 1-benzylazetidin-3-ol derivatives prepared by the process of the invention, as intermediates for the preparation of azetidine-3-carboxylic acid derivatives.

The invention is illustrated in the following Examples.

EXAMPLE 1

Preparation of 1-benzylazetidin-3-ol (1)

333 g of N-benzyl-3-amino-1-chloropropan-2-ol was taken up in 1665 ml of triethylamine and 10 g of tetrabutylammonium iodide was added. The resulting mixture was stirred under reflux for 13 hours, after which it was cooled, the hydrochloride precipitate filtered off and the filtrate washed twice with triethylamine. The combined filtrates were evaporated to yield 252 g of an oil, which was crystallized from 250 ml of toluene and 50 ml of hexane to yield 180.8 g of 1 as white crystals, m.p.: 66°–67° C., being a yield (based on aminopropanol) of 66.5%.

EXAMPLE 2

Use of 1-benzylazetidin-3-ol to prepare azetidine-3-carboxylic acid (a) 5.0 g of 1, 3.52 g of methanesulphonyl chloride and 6 ml of triethylamine in 40 ml of dichloromethane were stirred together for 18 hours. The mixture was filtered and the solvent was evaporated under reduced pressure. The residue was purified by chromatography on silica gel using isopropanol in dichloromethane as eluent to give the mesylate of 1-benzylazetidin-3-ol (2A), yield 4.25 g.

(b) 1.7 g of 2A, and 1.2 g of sodium cyanide were stirred together in 1 ml of water and 20 ml of dimethylformamide at 60° C. for 16 hours. The solvent was evaporated under reduced pressure and the residue was purified by chromatography on silica gel using isopropanol in dichloromethane as eluent to give 1-benzyl-3-cyanoazetidine (2B), yield 0.5 g.

(c) 0.5 g of 2B in 10 ml of saturated barium hydroxide solution was heated under reflux for 30 hours. The mixture was cooled, saturated with gaseous carbon dioxide and filtered. The solvent was removed from the filtrate under reduced pressure to give 1-benzylazetidine-3-carboxylic acid (2C), in 80% yield.

(d) 0.5 g of 2C in 15 ml of methanol was hydrogenated in the presence of a 5% palladium on carbon catalyst at room temperature. The catalyst was filtered off and the solvent was evaporated from the filtrate under reduced pressure to give azetidine-3-carboxylic acid in 90% yield.

EXAMPLE 3

Procedures similar to that of Example 1 were carried out, but omitting the tetrabutylammonium iodide, and also replacing that phase transfer catalyst by the bromide and by sodium iodide. In all cases a comparable yield of product could be achieved (around 65%), though longer reaction times were required.

COMPARATIVE EXPERIMENTS

The procedure of Example 1 was repeated, except that in step (b) the triethylamine was replaced with tributylamine, tripropylamine, diisopropylethylamine, pyrrolidine, pyridine or with 2,6-lutidine. In no case did the reaction produce any significant yield of the azetidinol, thus clearly demonstrating the unexpected specificity of triethylamine in promoting a high yield of that product.

We claim:

1. A process for the preparation of 1-benzylazetidin-3-ol that comprises the step of cyclizing N-benzyl-3-amino-1-chloro-propan-2-ol, in solution in triethylamine and optionally in the presence of a phase transfer catalyst.

2. A process defined in claim 5 wherein the cyclization is carried out in the presence of a phase-transfer catalyst.

3. A process as defined in claim 2 wherein the phase-transfer catalyst is a tetraalkylammonium halide.

4. A process as defined in claim 1 wherein the cyclization is effected by heating a mixture of the reagents at a temperature from 50° to 150° C.

5. A process as claimed in claim 4 wherein the cyclization is carried out under reflux.

* * * * *